United States Patent [19]

Balschmidt et al.

[11] Patent Number: 5,157,021

[45] Date of Patent: * Oct. 20, 1992

[54] INSULIN DERIVATIVES AND PHARMACEUTICAL PREPARATIONS CONTAINING THESE DERIVATIVES

[75] Inventors: Per Balschmidt, Espergaerde; Finn B. Hansen, Copenhagen, both of Denmark

[73] Assignee: Novo Nordisk A/S, Gentofte, Denmark

[*] Notice: The portion of the term of this patent subsequent to Jul. 2, 2008 has been disclaimed.

[21] Appl. No.: 630,835

[22] Filed: Dec. 20, 1990

Related U.S. Application Data

[62] Division of Ser. No. 2,672, Jan. 28, 1987, Pat. No. 5,028,586.

[30] Foreign Application Priority Data

Mar. 15, 1985 [DK] Denmark ................ 1197/85

[51] Int. Cl.$^5$ ............... A61K 37/02; A61K 37/26; C07K 7/40
[52] U.S. Cl. ............................... 514/3; 514/4; 514/866
[58] Field of Search ............... 530/303; 514/3, 4, 866

[56] References Cited

U.S. PATENT DOCUMENTS

| | | | |
|---|---|---|---|
| 3,903,068 | 9/1975 | Ruttenberg | 530/303 |
| 4,320,196 | 3/1982 | Morihara et al. | 435/70 |
| 4,320,197 | 3/1982 | Morihara et al. | 435/70 |
| 5,028,586 | 7/1991 | Balschmidt | 514/3 |

FOREIGN PATENT DOCUMENTS

146482B 10/1983 Denmark .
147437B 8/1984 Denmark .

OTHER PUBLICATIONS

F. Marki et al., *Hoppe-Seyler's Z. Physiol. Chem.*, Bd. 360. S. 1619–1632, 1979.
Daniel Levy, *Biochimica et Biophysica Acta*, 310 (1973), pp. 406–415.

*Primary Examiner*—F. T. Moezie
*Attorney, Agent, or Firm*—Dann, Dorfman, Herrell and Skillman

[57] ABSTRACT

Insulin derivatives in which from two to four amino acid residues of positions, A4, A17, B13 and B21 comprise an uncharged side chain and pharmaceutical preparations containing these insulin derivatives. The disclosed insulin derivatives and preparations possess protracted insulin activity. The protracted insulin activity is relatively insensitive to tryptic activity.

16 Claims, No Drawings

INSULIN DERIVATIVES AND PHARMACEUTICAL PREPARATIONS CONTAINING THESE DERIVATIVES

This is a division, of application Ser. No. 002,672, filed Jan. 28, 1987, now U.S. Pat. No. 5,028,586.

TECHNICAL FIELD

The present invention relates to novel insulin derivatives and to insulin preparations showing protracted action and comprising at least one of the novel insulin derivatives and, if desired, a fast acting insulin.

BACKGROUND ART

In severe or chronic cases the disease of Diabetes is usually treated with injection preparations containing insulin, e.g. porcine insulin, bovine insulin or human insulin.

Soluble insulin preparations are usually fast acting, but in return the action ceases after few hours. Therefore, it is necessary to give frequent injections, normally several times a day.

In order to overcome this disadvantage insulin preparations with protracted action have been formulated so that the action is maintained for several hours or even up to 24 hours or longer. Using such protracted preparations some diabetic patients only have to receive a small number of injections, e.g. a single or two injections during 24 hours.

Such a protracted action can be achieved by converting the insulin to a slightly soluble salt, such as zinc insulin or protamin insulin. The slightly soluble insulin salts are used in the form of suspensions from which the insulin is gradually released e.g. after subcutaneous injection.

Recently other methods have been invoked to achieve a protracted action. An example hereof is the encapsulation of insulin crystals in polymerized serum albumin. Another example is continuously acting infusion devices, so-called insulin pumps, which however may be uncomfortable and entail a risk to the patient.

The specifications of Danish patent application Nos. 3582/84, 3583/84 and No. 3757/84 disclose the preparation and use of insulin derivatives wherein the C-terminus of the B-chain is extended with an organic group carrying at least one positive charge, preferably Arg-OH or Arg-Arg-OH. Preparations containing suspensions of such insulin derivatives exhibit a protracted action.

However, the preferred methods for preparing the insulin derivatives disclosed in the specification of Danish patent application No. 3582/84 in an industrial scale involve the use of trypsin-like enzymes which implies that enzymatic activity may contaminate the final preparations, cf. examples of execution in the specification of Danish patent application No. 3757/84. The protracted action of the above-mentioned insulin derivatives wherein the C-terminus of the B-chain is extended with an organic group carrying at least one positive charge results exclusively from the extension of the B-chain. However, the extended B-chain is sensitive to enzymes which cleave the B-chain, especially at B29-lysine, and consequently, the protracted action may be reduced and even abolished. This enzymatic cleavage can also take place after subcutaneous injection, cf. the specification of Danish patent application No. 3583/84, page 15, line 18. As a result of the enzymatic activity the protracted action of the preparations containing the above-mentioned insulin derivatives wherein the C-terminus of the B-chain is extended with an organic group carrying at least one positive charge may vary considerably.

DISCLOSURE OF THE INVENTION

It has now surprisingly been found that by the use of insulin derivatives, wherein one or more of the four amino acid residues of positions A4, A17, B13 and B21 comprise an uncharged side chain, in insulin preparations, in particular injection preparations, a hitherto unknown and desirably long-lasting protracted action is achieved.

Accordingly, the invention relates to insulin derivatives wherein one or more of the four amino acid residues of positions A4, A17, B13 and B21 comprise an uncharged side chain.

The invention relates specifically to insulin derivatives wherein one or two of the four amino acid residues of positions A4, A17, B13 and B21 comprise an uncharged side chain.

The invention relates in particular to insulin derivatives in which one of the four amino acid residues of positions A4, A17, B13 and B21 comprises an uncharged side chain.

The invention relates particularly to insulin derivatives wherein the amino acid residue of position A4 comprises an uncharged side chain.

The invention relates specifically to insulin derivatives in which the amino acid residue of position A17 comprises an uncharged side chain.

The invention relates in particular to insulin derivatives wherein the amino acid residue of position A4 is a glutamine residue.

The invention relates specifically to insulin derivatives wherein the amino acid residue of position A17 is a glutamine residue.

The invention also relates to insulin preparations containing at least one insulin derivative wherein one or more of the four amino acid residues of positions A4, A17, B13 and B21 comprise an uncharged side chain and, if desired, also containing a fast acting insulin.

A particularly advantageous embodiment of the insulin preparation of the invention is an injection preparation exhibiting protracted insulin action and comprising a suspension of at least one insulin derivative of the invention in an isotonic aqueous medium having a neutral pH and optionally containing a buffer and/or a preserving agent and, if desired, a fast acting insulin.

Insulins which are normally used for the treatment of Diabetes, such as porcine, bovine, ovine, and human insulin, do all contain six free carboxylic groups, viz. in the A4-, A17-, A21-, B13-, B21- and B30-amino acid residues. The numbering is referring to the positions in the insulin A and B chain, respectively, starting from the N termini. The biological activity of insulin will usually decrease by an increasing degree of derivatization. However, the biological activity is influenced surprisingly little even at high degrees of derivatization of the free carboxylic acid groups but when all six free carboxylic acid groups are derivatized the biological activity is completely abolished, vide D Levy: Biochem. Biophys. Acta, 310 (1973), pages 406–415.

By means of the insulin preparations of the invention the insulin activity can be maintained, and at the same time a surprisingly protracted action can be achieved. This protracting effect is dependent on the properties of the specific derivative, e.g. the number of amino acid residues comprising an uncharged side chain and the chemical constitution of the uncharged side chain. Thus, it is possible to vary the protracted action at will. A considerable advantage and novel feature of the insulin derivatives of the invention is that the protracted action is relatively insensitive to tryptic activity irrespective of the origin of the tryptic activity.

In the case of Insulin-Dependent Diabetes a frequently used therapy consists in two daily injections of a protracted insulin preparation, one in the morning and one in the evening just before bedtime, in order to create a basic insulin level. Additionally, three injections of a fast acting insulin preparation are given prior to the principal meals. The disadvantage of this therapy is that the late injection of the protracted preparation may result in a dangerously low blood glucose level in the course of the night. This situation may be avoided by injecting a mixed preparation of a protracted and a fast acting insulin before supper, whereby hypoglycemia will, if at all, occur during the evening, where it can be averted by means of a light snack. However, this type of the therapy often results in hyperglycemia during the morning, as the most used protracted insulin preparations "Insulatard" ® and "Monotard" ® do not act long enough. Therefore, it is desirable to provide the diabetic patient with insulin preparations that act longer than the preparations commonly in use, in particular if one injection of such preparations will suffice for one or even several days. Insulin preparations prepared according to the invention exhibit a protracted insulin action of the same or longer duration than that of the commonly used protracted insulin preparation "Insulatard" ®.

The invention relates in particular to the following specific compounds:
Human insulin-A4-gln
Porcine insulin-B21-gln
Human insulin-B13-gln
Human insulin-(A17,B21)-gln
Human insulin-A4-ala
Human insulin-B21-thr
Human insulin-B13-val
Human insulin-B21-thr-A17-gln
Human insulin-B21-methyl ester
Human insulin-A17-methyl ester When the insulin preparations of the invention contain a fast acting insulin, this insulin may e.g. be human or porcine insulin.

By use of porcine, bovine, ovine, rabbit, or in particular human insulin, the insulin derivatives of the invention can be prepared in a manner known per se for the conversion of a carboxylic acid group into an uncharged group, e.g. by esterification or amidation. Thus, an insulin derivative wherein one or more of the carboxylic acid groups of positions A4, A17, B13 and B21 are methylated, is e.g. prepared by reacting human insulin-B30-methyl ester in borontrifluoride/methanol for a suitable time, followed by fractionation of the modified insulin derivatives on an anion exchange column at a slightly basic pH value. The products are fractionated and isolated by preparative HPLC, whereafter the B30 methyl ester group is removed by gentle hydrolysis in an ice-cold solution of 0.1N sodium hydroxide.

The preparation of the insulin derivatives of the invention wherein one or more amino acid residues of positions A4, A17, B13 and B21 comprise an uncharged side chain can be carried out by use of biotechnological methods. Thus, some or all or the glutamic acids located at these positions may be replaced by naturally occuring amino acids carrying an uncharged side chain, such as glutamine.

The preferred method to prepare these modified insulins is by biosynthesis, as by e.g. changing only a single base in the codon in the DNA strand coding for glutamic acid this codon can be made code for glutamine. By changing bases in the DNA strand coding for insulin (or proinsulin) it is thus possible to make modifications which would be difficult or impossible to make chemically due to limitations as to isolation.

There exists a number of different methods to prepare human insulin by biosynthesis. It is common to all of them that the DNA strand coding for either the entire proinsulin, a modified version thereof or the A- and B-chain separately has been inserted into a replicable plasmide containing a suitable promotor. By transforming this system into a given host organism a product can be produced, which can be converted into authentic human insulin in a manner known per se.

Some known methods for biosynthesis of proinsulin or A- and B-chain and their conversion into insulin are described below.

In the well known Genentech process an intracellular preparation in *E. coli* of polypeptides is made, wherein these polypeptides are a fusion between β-galactosidase and the A- and B-chain, respectively, of insulin. After fermentation the two products are isolated, the A- and B-chains are split off from β-galactosidase by means of cyanogen bromide, whereafter the sulphitated chains are combined under reducing conditions in the presence of dithiothreitol at a pH value of 10.5. Finally human insulin is isolated from this reaction mixture.

In the process disclosed in EPO 55945 the product is synthetized as a fusion protein with another protein separated by a cleaving site. This may be a protease cleaving site or a site which can be cleaved chemically (e.g. methionine). The gene for proinsulin is e.g. cloned as a genefusion with another protein by means of recombinant DNA techniques. After isolation, the chimeric protein is cleaved by using a suitable enzyme or CNBr, whereupon the denatured proinsulin is isolated in a sulphitolyzed form. This product is renatured under reducing conditions using β-mercapto ethanol at a pH of 10.5, as described by Frank, followed by trypsin/CpB cleavage as described by Kemmler (1971). The resulting insulin is isolated in a manner known per se.

Finally, proinsulin can be prepared biosynthetically by using the method disclosed in EPO 116201. In this method proteins are secreted into the culture medium by using the α-factor system from Saccharamyces cerevisiae. By inserting the gene coding for proinsulin into this system, proinsulin can be isolated from the culture medium by using the system described in Danish patent application No. 3091/84. Hereafter, proinsulin can be converted into insulin by the known methods described above.

In the above, methods are described in which the product is either proinsulin or A- or B-chain separately. Furthermore, these products are either synthetized together with a signal sequence, the purpose of which is to bring the product through to the cell surface where it is split, or as a fusion with a protein, the purpose of which is to stabilize the product.

Moreover it is possible to prepare modified proinsulins biosynthetically. European patent application No. 82303071.3 discloses proinsulins wherein the C-chain is modified by means of recombinant DNA techniques.

The above-mentioned modifications of insulin can be prepared by expressing the modified DNA sequence in a suitable expression system. The changes of the DNA sequence can be made by in vitro mutagenesis of the insulin gene by a method described by Thomas A. Kunkel, Proc. Natl. Acad. Sci., USA, Vol 82, pp. 448–492 (1985). According to this method the insulin gene is cloned into the single-stranded DNA bacteriophage M13. DNA from this phage is purified, and hereto a primer, typically a 15–25-mer, which contains the given mutation (one mismatch) as well as a homology on each side of this mutation is annealed. The primer is then extended by use of a DNA polymerase in the total length of the phagegenome and thus provides the complete double-stranded molecule, wherein one strand contains the mutation, and the other contains the wild type gene. By introducing this molecule into an *E. coli* cell, the phage progeny will partly be phages containing the wild type gene, partly phages containing the mutation. Among these phages it is then possible to screen for the desired type by hybridization with the mutagenization primer to single-stranded DNA of the phage progeny. The primer will have a complete homology to the mutated strand, but will be different from the wild type at a single nucleotide. After screening double-stranded DNA can be isolated from the *E. coli* cells, wherein the phage is replicated, and the modified insulin gene can be isolated herefrom. This gene is thereafter reinserted into the original expression system.

The injection preparations can comprise the insulin derivatives of the invention as amorphous and/or crystalline suspensions, either separately or in combination with other such insulin derivatives and/or naturally occurring insulins. It has been found that a majority of these derivatives can be crystallized with zinc, either at a pH value being higher than their isoelectric points, or at a pH value about the isoelectric pH value, when the crystallization medium contains a phenol. It is also possible to crystallize the insulin derivatives of the invention in the presence of protamin or an excess of zinc, which causes a further protracted activity.

MODES FOR CARRYING OUT THE INVENTION

The invention is further illustrated by means of the following examples.

EXAMPLE 1

Preparation of human insulin-B21-methyl ester 500 mg of human insulin-B30-methyl ester were suspended in 50 ml of dry methanol. 2.0 ml of 20% w/v borontrifluoride/-methanol were added with stirring. After standing at ambient temperature for 2 hours the suspension was poured into 400 ml of ether and centrifuged at 2500 × g at 4° C. for 20 minutes. The precipitate was washed twice with ether, resuspended in 150 ml of ether, evaporated in vacuo and dissolved in 50 ml of 20 mM TRIS/HCl, 60% by volume ethanol, pH 8.25. The sample was then applied to a 1.6×21 cm Q-Sepharose® CL-6B Fast Flow column equilibrated with the same buffer. After 1 hour of isocratic elution at a flow rate of 24 cm/hour the column was eluted with a sodium chloride gradient that increased form 0 to 0.1M over the next 16 hours. The insulin dimethyl ester peak was divided into 3 main pools. The pool eluted first was further fractionated on a 4×250 mm LiChrosorb® RP18 column (Merck 50333) equilibrated with 0.125M ammonium sulphate, pH value 4.0 and 38% by volume acetonitrile at 45° C. After applying 1–2 mg of insulin dimethyl ester, the protein main fraction eluted at 20–25 minutes at a flow rate of 12 cm/min.

10 mg of the insulin dimethyl ester thus obtained were dissolved in 1 ml of ice-cold 0.1N sodium hydroxide solution. The reaction mixture was allowed to stand at 0° C. for 5 minutes, whereafter the pH value was adjusted to 9 with hydrochloric acid. The mixture was applied to a 0.5×5 cm Mono Q® anion exchanger column and fractionated for 30 minutes in 20 mM TRIS/HCl, 60% by volume ethanol, pH 8.25 with a linear sodium chloride gradient increasing to 0.1M at a flow rate of 5.1 cm/min. After removal of the ethanol in vacuo from the fraction containing human insulin-B21-methyl ester, the protein was precipitated at a pH value of 6.3. Yield: 7 mg.

The human-B21-methyl ester was characterized by Plasma Desorption Mass Spectrometry showing the correct molecular weight and by decomposition with S. Aureus protease, whereby the B21 ester position was confirmed.

EXAMPLE 2

Preparation of human insulin-A17-methyl ester

Human insulin-A17-methyl ester was isolated and identified as described in Example 1, however the second eluted insulin dimethyl ester pool isolated from the anion exchange chromatographical step was used for further fractionation. Hereby 6.5 mg of human insulin-A17-methyl ester were obtained.

EXAMPLE 3

Formulation and biological effect of a preparation containing human insulin-B21-methyl ester 25 ml of a medium containing 1.6% (w/v) of glycerol. 0.33% (w/v) of m-cresol, 1/75M of sodium phosphate, pH value 7.3, were prepared. The solution was sterilized by filtration. 1.5 mg of human insulin-B21-methyl ester, prepared as described in Example 1, were suspended in 1.0 ml of medium.

A protracted hypoglycemia was observed in guinea pigs after subcutaneous administration of this zinc-free preparation. The resulting protracted insulin action is comparable to the hypoglycemia observed after injection of a standard protamin insulin preparation "Insulatard" ®.

EXAMPLE 4

Formulation and biological effect of a crystalline insulin preparation containing human insulin-A17-methyl ester 4.5 mg of human insulin-A17-methyl ester were dissolved in 2.7 ml of 0.015M phosphoric acid. 21 mg of sodium chloride and 4.1 µlitres of an aqueous solution of 152 mM zinc chloride were added. The solution was sterilized by filtration. The pH value of the solution was adjusted to 8.0 under aseptic conditions with a sterile aqueous solution of sodium hydroxide. The pH value of the solution was then readjusted to 7.3 with sterile hydrochloric acid, and rhombohedral crystals with a mean size of 10 um were formed with gentle stirring at 21° C. The volume was adjusted to 3 ml with sterile water.

Moreover, a sterile solution of 3 ml of 13.5 mM phosphoric acid in admixture with 21 mg of sodium chloride and 9 µlitres of m-cresol was prepared, and the pH value was adjusted to 7.3 with a sterile aqueous solution of sodium hydroxide. The two solutions were combined.

Such a solution induces strongly protracted hypoglycemia in guinea pigs at a dosage of 18 μg/kg. The protracted insulin action obtained is longer than the protracted action of the known injection preparation "Insulatard" ®. The area below the blood glucose curve indicates that the insulin derivative exhibits nearly the same biological activity as human insulin.

EXAMPLE 5

Preparation of human insulin-A4-gln 150 mg of human proinsulin-A4-gln, produced by one of the biosynthetic methods described above, was dissolved in 30 ml of TRIS/hydrochloride, pH value 7.5, containing 3 mg of matrix-bound trypsin (Trypsin-Sepharose ® Fast Flow). The mixture was allowed to stand at room temperature for 1 hour, after which the resin was removed by filtration. The resulting des-B30-insulin-A4-gln was isolated by precipitation at a pH value of 6.3 and freeze-dried. The protein powder was dissolved in a mixture containing 200 mg of threonine methyl ester, 1000 μlitres of ethanol and 400 μlitres of distilled water. The pH value was adjusted to 6.3 with acetic acid, and 1 mg of matrix-bound trypsin was mixed in. After standing for 2 hours at room temperature with gentle agitation, the protein was precipitated after filtration by adding 10 volumes of 2-propanol. The dried precipitate was redissolved in 20 mM TRIS/hydrochloride, 60% by volume ethanol, pH value 8.25, applied to a 1.6×20 cm Q-Sepharose ® CL-6B Fast Flow column equilibrated with the said buffer and eluted with a linear sodium chloride gradient increasing from 0 to 0.1M over 15 hours at a flow rate of 24 cm/h. The ethanol was removed in vacuo from the fraction containing A4-gln-human insulin-B30-methyl ester, and the protein was precipitated by adjusting the pH value to 6.8. The B30-methyl ester was hydrolyzed for 10 minutes in cold 0.1M sodium hydroxide at a protein concentration of 10 mg/ml followed by adjustment of the pH value to 8.25. The protein solution was applied to a 1.6×20 cm Q-Sepharose ® CL-6B Fast Flow column after dilution with 2 volumes of 20 mM TRIS/hydrochloride, pH value 8.25, and eluted as described above. The protein was precipitated at a pH value of 6.3 after removal of the ethanol. 30 mg of human insulin-A4-gln was obtained after freeze-drying.

The purity of the product was ascertained by reverse phase high pressure liquid chromatography, and the identity of the product was confirmed by amino acid analysis, multistep Edman-degradation and plasma desorption mass spectrometry.

EXAMPLE 6

15 mg of human insulin-A4-gln, obtained as described in Example 5, was dissolved in 10 ml of a solution containing 13.5 mM phosphoric acid, 0.3% m-cresol and 1.6% glycerol. The solution was sterilized by filtration, and the pH value was adjusted to 9,0 with a sterile aqueous solution of sodium hydroxide. The pH value was readjusted to 8.2 with a sterile solution of hydrochloric acid, and human insulin-A4-gln crystallized as rhombohedral crystals with gentle stirring.

By subcutaneous injection of this crystalline suspension into guinea pigs at 0.5 IU/kg, the resulting protracted hypoglycemic effect is nearly identical both in timing and amplitude to the hypoglycemic effect caused by injection of "Insulatard" ® at 0.5 IU/kg.

We claim:

1. Insulin derivative wherein from two to four amino acid residues of positions A4, A17, B13 and B21 comprise an uncharged side chain.

2. Insulin derivative according to claim 1, wherein two of the four amino acid residues of positions A4, A17, B13 and B21 comprise an uncharged side chain.

3. Insulin derivative according to claim 1, wherein the amino acid residue of position A4 comprises an uncharged side chain.

4. Insulin derivative according to claim 1, wherein the amino acid residue of position A17 comprises an uncharged side chain.

5. Insulin derivative according to claim 3, wherein the amino acid residue of position A4 is a glutamine residue.

6. Insulin derivative according to claim 4, wherein the amino acid residue of position A17 is a glutamine residue.

7. Insulin preparation possessing protracted insulin activity comprising at least one insulin derivative, wherein from two to four amino acid residues of positions A4, A17, B13 and B21 comprise an uncharged side chain and a physiologically compatible medium.

8. Insulin preparation according to claim 7, wherein two of the four amino acid residues of positions A4, A17, B13 and B21 comprise an uncharged side chain.

9. Insulin preparation according to claim 7, wherein the amino acid residue of position A4 comprises an uncharged side chain.

10. Insulin preparation according to claim 7, wherein the amino acid residue of position A17 comprises an uncharged side chain.

11. Insulin preparation according to claim 9, wherein the amino acid residue of position A4 is a glutamine residue.

12. Insulin preparation according to claim 10, wherein the amino acid residue of position A17 is a glutamine residue.

13. Insulin preparation according to claim 7, which also contains a fast acting insulin.

14. Injectable insulin preparation according to claim 7, exhibiting protracted insulin action, comprising a suspension of at least one insulin derivative in an isotonic aqueous medium having a neutral pH.

15. Insulin preparation according to claim 14, which includes a buffer, a preserving agent or a combination thereof.

16. Insulin preparation according to claim 14, which also contains a fast acting insulin.

* * * * *